United States Patent [19]

Kelley

[11] Patent Number: 4,829,129

[45] Date of Patent: May 9, 1989

[54] REACTION PRODUCT OF POLYMER WITH CHLORINE DIOXIDE

[75] Inventor: Joseph M. Kelley, Westfield, N.J.

[73] Assignee: International Dioxcide, Inc., Clark, N.J.

[21] Appl. No.: 55,337

[22] Filed: May 29, 1987

[51] Int. Cl.$^4$ .................. A61K 31/79; A01N 59/00; A01K 33/20
[52] U.S. Cl. .................. 525/326.9; 424/662; 424/80
[58] Field of Search .................. 424/79, 80, 149; 525/326.9

[56] References Cited

U.S. PATENT DOCUMENTS

| | | | |
|---|---|---|---|
| 2,739,922 | 3/1956 | Shelanski | 424/78 |
| 4,499,077 | 2/1985 | Stockel et al. | 514/635 |
| 4,654,208 | 3/1987 | Stockel et al. | 514/252 |
| 4,731,193 | 3/1983 | Mason et al. | 422/29 |

Primary Examiner—Joseph L. Schofer
Assistant Examiner—Peter F. Kulkosky
Attorney, Agent, or Firm—Burns, Doane, Swecker & Mathis

[57] ABSTRACT

Provided is a novel composition which is the reaction product of chlorine dioxide and a polymer, and in particular, polymeric N-vinyl-α-pyrrolidone. The resulting product is an organically stabilized $ClO_2$ composition which is a powerful microbiocide.

21 Claims, No Drawings

4,829,129

REACTION PRODUCT OF POLYMER WITH CHLORINE DIOXIDE

BACKGROUND OF THE INVENTION

1. Field of the Invention

This invention relates to a novel composition obtained upon the reaction of chlorine dioxide ($ClO_2$) with a polymer, preferably polymeric N-vinyl-α-pyrrolidone.

2. Brief Description of the Prior Art

Chlorine dioxide is a gas which is explosive in air at concentrations over 9 to 10%. It has some solubility in water, but solutions of chlorine dioxide in water rapidly lose $ClO_2$ at atmospheric pressure and ambient temperature. Thus the effectiveness of solutions of $ClO_2$, although possessing a powerful killing effect on bacteria, fungi, viruses, spores, etc., is fugitive to some extent due to the tendency for loss of $ClO_2$ gas from the solution.

One approach to this stability problem has been to stabilize the $ClO_2$ solution with various inorganic salts, as described in U.S. Pat. No. 2,701,781, at a pH above 8 and to liberate $ClO_2$ slowly by reducing the pH of the stabilized solution. This approach has disadvantages, however, in that it requires an operation to lower the pH and the resulting solution exhibits a tendency to lose free $ClO_2$ once it is liberated from the stabilized solution. There is, therefore, a need for a chlorine dioxide solution of improved stability.

The use of polymeric N-vinyl pyrrolidone for stabilizing halogen containing solutions s disclosed in U.S. Pat. No. 2,739,922. Reaction products of $ClO_2$ with polymers such as polymeric N-vinyl pyrrolidone to provide an organically stabilized $ClO_2$ composition, however, are nowhere disclosed or suggested therein.

Accordingly, it is an object of the present invention to provide a novel, stabilized composition of $ClO_2$.

It is another object of the present invention to provide an organically stabilized composition of $ClO_2$.

Still another object of the present invention is to provide an organically stabilized $ClO_2$ composition which is a powerful microbiocide.

These and other objects of the present invention will become apparent to those skilled in the art, as well as the scope, nature and utilization, upon a review of the following description and the claims appended hereto.

SUMMARY OF THE INVENTION

In accordance with the foregoing objectives, the present invention provides a very stable and powerful microbiocide which is the reaction product of gaseous chlorine dioxide and a polymer, most preferably polymeric N vinyl-α-pyrrolidone (PVP). In preparing the product, it is believed that rather than a complexing of the $ClO_2$ with a polymer such as PVP, a definite chemical reaction between $ClO_2$ and PVP occurs. This is evidenced by the fact that any resulting aqueous solution is colorless and the pH of the solution is reduced below 2.0. For example, a 20% PVP solution is initially at a pH of 4, but after reaction with $ClO_2$, the pH of the solution is decreased to 1.5.

DETAILED DESCRIPTION OF THE PREFERRED EMBODIMENTS

Typical polymeric N-vinyl-α-pyrrolidone compounds useful herein for reacting with chlorine dioxide are the polymeric N-vinyl-α-pyrrolidones of the type described in U.S. Pat. No. 2,265,450. The water soluble polymers of N-vinyl-α-pyrrolidone as a class are effective in this invention and the degree of polymerization (i.e. molecular weight of the polymer) has no apparent effect on the reaction. However, for any particular use, polymers of a specific molecular weight range may be preferred for various reasons. The Fichentscher K value is a convenient designation of relative degree of polymerization or relative molecular weight and will therefore be used to designate the specific polymers.

For example, polymers having a K value below 15, and particularly below 10, are rapidly excreted from the body in the urine when administered in parenteral fluids. Thus, such polymers are useful when it is desired to prepare the cidal composition and to have that compound excreted from the body more slowly. Moreover, the osmotic pressure of solutions of polymers within this range of K values appears to be better suited for the preparation of parenteral fluids. Therefore, such molecular weight polymers are usually preferred in compositions intended for use in parenteral fluids, or where it is desired to prolong the presence and effect of the composition in the body.

The higher polymers, i.e. those having a K value above 50, and especially above 75, to e.g., 90, appear to be stored in the liver for appreciable periods of time. Such high molecular weight products may, therefore, be preferred in compositions intended for therapy of the liver.

The water soluble polymers of N-vinyl pyrrolidone have been extensively employed as blood plasma substitutes and appear to be entirely innocuous, having $LD_{50}$ values in the range of 100 gm/kg. While for certain purposes, as discussed above, a polymer for a particular weight range may be desired, the cidal effect does not appear to be related to the molecular weight. Thus, the range of molecular weight of a particular polymer to be employed in any given application will be governed by considerations other than the cidal action. Such considerations are well known in the medical profession and the proper choice of polymer may readily be made. For external use, the molecular weight (K value) of the polymer appears to be without effect, save for its effect on the viscosity of the composition.

The novel cidal composition of the present invention is generally prepared by dissolving solid polyvinyl pyrrolidone (K 10 to K 90) in water to make solutions ranging from 1% to 60% by weight of the PVP (depending upon its molecular weight), saturating this solution with $ClO_2$, and allowing the $ClO_2$ to react with the PVP at room temperature and atmospheric pressure until the yellow-chartreuse color of the chlorine dioxide has disappeared. The procedure may be repeated several times, with the solution being allowed to sit until colorless. The colorless solution is then assayed to determine the equivalent free $ClO_2$ which has been incorporated into the PVP solution and which is available as an oxidizing biocide. Incorporation of higher concentrations into water causes the solution to become very viscous and hard to handle, especially at higher K values. However, the PVP is still reactive and, in fact, solid PVP shows reactivity towards $ClO_2$ gas. Thus, reaction in the solid state is possible.

The effective concentration of $ClO_2$ or chlorous acid in an aqueous solution of the present composition is easily measured by reacting the solution with KI thus liberating $I_2$ in proportion to the oxidizing power of the solution (due to $ClO_2$ or chlorous acid). The $I_2$ is then titrated with sodium thiosulfate. This method is well known and conventionally used in the assay of chlorine dioxide solutions.

If desired, the pH of the biocidal solution containing the PVP-chlorine dioxide reaction product may be raised by reaction with organic bases, such as amines, without appreciably affecting the biocidal activity of the solution.

Alternative methods for preparing the $ClO_2$/PVP solution would be the generation of $ClO_2$ in a solution of PVP by known methods, such as the reduction of chlorate ion, or the oxidation of chlorite ion, by any of the known methods already described in the chemical literature.

Exemplary polymers capable of forming the same type of complex or reaction product with $ClO_2$ besides PVP include water soluble copolymers of vinylpyrrolidone with vinyl pyridine, acrylamide, substituted acrylamides, vinyl caprolactam, vinyl phthalamide, etc. Also homopolymers such as polyvinyl caprolactam, polyvinyl-α-valerolactam, polyvinyl-α-valerolactam, and the like. These polymers are expected to exhibit the same type of behavior to a greater or lesser degree depending upon the particular polymer chosen.

The cidal solutions of the present invention are useful as a wide spectrum biocide against such organisms as bacteria, fungi, viruses, protozoa, yeast, spores, and the like. Applications which take advantage of the killing power of such solutions are infections of the skin, toes, hands, ears and, after adjustments to higher pH, gingivitus, burns, decubitus ulcers, dermatitis, varicose ulcers, thrush, skin grafting, and the like. The composition of the present invention is particularly useful in applications which can take advantage of the film forming qualities of the PVP to protect areas from external contamination, coupled with the antiseptic power of the $ClO_2$ reaction product such as wounds, burns, skin infections, etc. Application of the composition results in more rapid healing.

The reaction product of PVP with $ClO_2$ may be administered topically as a powder, ointment, gel, spray or solution.

The $ClO_2$ compositions of the present invention may also be formulated with a wide variety of surface active agents such as soap or alkylaryl sulfate and sulfonate, higher fatty alcohol sulfates and sulfonates, cationic agents such as quaternary ammonium compounds, and non-ionic surface active agents such as higher fatty alcohols or the polyglycol ether esters of higher fatty acids, to produce valuable sanitizers which have a wide field of application in cleaning and sanitizing operations such as washing, bathing, spraying, dipping, and the like. Surface active agents such as the Tweens and Ammonyxs are particularly suitable for use with the compositions of the present invention. Compositions containing stabilized chlorine dioxide, quaternary ammonium compounds, and the present reaction product of $ClO_2$ with polymeric N-vinyl pyrrolidone show a killing power on microorganisms far in excess of that expected for the sum of the components in the composition. The same results apply to mixtures of stabilized $ClO_2$ and the compositions of this invention.

To prevent the loss of equivalent $ClO_2$ content, solutions can be supplied with an excess of free $ClO_2$. This excess $ClO_2$ will enhance the microbiological activity of the solution initially but will slowly evaporate when the solution is exposed to the air, leaving only the bound $ClO_2$ (equivalent).

The following examples are provided to illustrate the preparation of a biocidal composition in accordance with the present invention, but are not intended to limit the scope of the invention in any manner.

It should be noted that in the examples which follow, the highest equivalent oxidizing power of the solutions is 2200 ppm equivalent $ClO_2$, which would give the solution of Example 15 a dilution of approximately 1:7 with water. Higher levels of equivalent free $ClO_2$ can be prepared by increasing the reaction temperature (although $ClO_2$ is less soluble in the solution as the temperature is raised) and/or the reaction pressure to increase the concentration of $ClO_2$ in the liquid phase. Other methods of increasing the extent of reaction between PVP and $ClO_2$ are multiple cycles which may be employed to obtain higher levels of equivalent $ClO_2$ content.

Moreover, as illustrated in the following examples, the pH of the solution of PVP is about 1.5 after reaction with $ClO_2$. The pH may be adjusted to higher values by adding bases without substantially altering the cidal properties of the composition. Among the applications well suited for this adjusted material are dental sterilization and animal medicine.

EXAMPLES 1–4

Polymeric N-vinyl-α-pyrrolidone (K 15, 5% by weight) was dissolved in distilled water. $ClO_2$ gas from a generator was passed through the solution for several hours until it was saturated and became brilliant yellow-green in color. A sample of distilled water was saturated in the same manner to the same brilliant yellow-green color. The two solutions were then divided in half and one of the two solutions was capped (i.e. closed) and the other was left open to the atmosphere to allow $ClO_2$ gas to slowly escape from solution. All samples were assayed from time to time using the KI-sodium thiosulfate method. The results are recorded below in Table I.

TABLE I

| Example No. | 1 | 2* | 3 | 4* |
|---|---|---|---|---|
| Sample | 5% PVP | Distilled $H_2O$ | 5% PVP | Distilled $H_2O$ |
| Initial Color | ←bright yellow-green→ | | | yellow |
| State | open | open | closed | closed |
| Time - 6 Days: | | | | |
| Color | nearly colorless | water white | brilliant yellow-green | pale yellow |
| Free $ClO_2$, ppm | 108 | 5 | 170 | 5 |
| Time - 39 days: | | | | |
| Color | water white | water white | bright yellow-green | pale yellow |
| Free $ClO_2$, ppm | 105 | 2 | 170 | 37 |

*Comparative

The above data shows that the open solution of PVP designated Example I, although colorless after 39 days (indicating no free $ClO_2$ present), had an equivalent $ClO_2$ content of 105 ppm. The open solution of distilled water (designated Example 2), was also water-white but had lost all of its $ClO_2$ content. The closed samples of PVP and distilled water (designated as Examples 3 and 4) retained some free $ClO_2$ as evidenced by their color and analysis.

EXAMPLES 5–8

Another series of samples was prepared by dissolving 10% by weight of PVP (K 15) in distilled water and dividing the solution in half. One-half was held as a control and the other sample was saturated with $ClO_2$ and allowed to react. In like manner, two distilled water samples were prepared, one being saturated with $ClO_2$ and the other being held as a control. All samples were tightly capped and analyzed at various intervals for their total $ClO_2$ content by the KI-sodium thiosulfate method. Free $ClO_2$ in the yellow solution was determined by a UV Spectrophotometer at 390 nm. Combined $ClO_2$ was calculated by subtracting free $ClO_2$ from total $ClO_2$. In a colorless solution of the PVP - $ClO_2$ reaction product at pH 1.5, the KI - sodium thiosulfate method gives total $ClO_2$ which is equal to free $ClO_2$ (equivalent) or bound $ClO_2$. The results are recorded below in Table II.

TABLE II

| Example No. | 5* | 6 | 7** | 8** |
|---|---|---|---|---|
| Sample composition | 10% PVP | 10% PVP + $ClO_2$ | Dist. $H_2O$ | Dist. $H_2O$ + $ClO_2$ |
| Time-0 days: | | | | |
| Free $ClO_2$, ***ppm | 0 | 567 | 0 | 387 |
| Combined $ClO_2$, ppm | 0 | 1529 | 0 | 1934 |
| Time-5 days: | | | | |
| Free $ClO_2$, ***ppm | 1.3 | 742 | 0 | 418 |
| Combined $ClO_2$, ppm | 0 | 121 | 0 | 1580 |
| Total $ClO_2$, ppm | 1.3 | 863 | 0 | 1997 |
| Time-14 days: | | | | |
| Free $ClO_2$, ***ppm | 0 | 308 | 0 | 189 |
| Combined $ClO_2$, ppm | 0 | 0 | 0 | 606 |
| Total $ClO_2$, ppm | 0 | 308 | 0 | 795 |
| Color | orange | very pale yellow | water white | brilliant yellow-green |
| pH | 4.1 | 1.9 | 6.2 | 3.1 |
| Odor | slight alcoholic | iodine like | none | very strong $ClO_2$ |

*Control
**Comparative
***Equivalent

The above data shows that a reaction has taken place between the PVP and $ClO_2$ in Example No. 6 as evidenced by the decrease in pH from 4.1 to 1.9, a decrease in color of the solution, and the absence of the characteristic odor of chlorine dioxide. In addition, the composition of Example No. 6, when assayed for $ClO_2$ by the KI-sodium thiosulfate method, gives an indication of $ClO_2$ equivalent of 308 ppm after 14 days.

A possible explanation for these observed facts is the reduction of $ClO_2$ to chlorous acid which is then stabilized by or complexed with the PVP present. Normally, chlorous acid is unstable and tends to form $ClO_2$. Here it does not decompose and is available in stable form for use as a biocide.

EXAMPLES 9-12

Two solutions of 10% by weight PVP (K 15) were prepared, and their pH was adjusted from 4.0 to 7.0 with NaOH. Both solutions were saturated with $ClO_2$ for 24 hours and assayed. One was adjusted back to pH 7.0. Both were resaturated with $ClO_2$ and assayed. This procedure was repeated 3 times and the solutions were allowed to decolorize for 11 days. Two samples of 25% by weight of PVP were also prepared and 0.5 wt % $NaClO_2$ was added to the solutions and the pH was lowered with acid to 4.0 and 2.4. The results are given in Table III.

TABLE III

| Example No. | 9 | 10* | 11 | 12 |
|---|---|---|---|---|
| % PVP | 10 | 10 | 25 | 25 |
| $ClO_2$ | Yes | Yes | No | No |
| $NaClO_2$, wt. % | 0 | 0 | 0.5 | 0.5 |
| Color | water-white | water-white | pale yellow | bright yellow-green |
| pH | 1.2 | 1.2 | 4.0 | 2.4 |
| Free $ClO_2$, **ppm | 567 | 532 | 243 | 353 |

*pH of Example 10 was readjusted back to 7.0 before each $ClO_2$ saturation.
**Equivalent The results show that 530-560 ppm of equivalent $ClO_2$ result from successive saturations of 10% PVP solutions with chlorine dioxide, and that the PVP-$ClO_2$ reaction product results from chlorite acidification.

EXAMPLES 13 AND 14

A 10% PVP (K 15) aqueous solution was saturated with chlorine dioxide and was then divided into equal portions and capped. One solution was stored in the dark for 12 days and the other was exposed to strong sunlight for 12 days. Both were then assayed. The results are recorded in Table IV.

TABLE IV

| Example No. | 13 | 14 |
|---|---|---|
| % PVP | 10 | 10 |
| Days Exposure | 12 | 12 |
| UV light | no | yes |
| Color | ← water-white → | |
| pH | 1.7 | 1.6 |
| Free $ClO_2$, *ppm | 455 | 43 |

*Equivalent

The above data indicates that ultraviolet radiation does not enhance the reaction between PVP and $ClO_2$. In fact, it is known to destroy $ClO_2$ and appears to be detrimental to the reaction product of $ClO_2$ and PVP, judging from the low equivalent $ClO_2$ content of the material exposed to UV radiation.

EXAMPLES 15 AND 16

A 20% by weight PVP (K 15) solution was prepared by dissolving the PVP in 200 grams of tap water. A 50 gram aliquot of the above solution was saturated with $ClO_2$ over a period of 4 hours. Another 50 gram portion of the PVP solution was added to the first 50 gram portion and the total solution was then saturated with $ClO_2$. This procedure was repeated four times until the full 250 grams of the PVP solution had been reacted with $ClO_2$. This solution was then exposed to the atmosphere for 5½ days until it was water white, and then was assayed. The solution was again assayed 3½ days later. The results of the assays are recorded in Table V.

TABLE V

| Example No. | 15 | 16 |
|---|---|---|
| % PVP | 20 | 20 |
| Days Stored | 5.5 | 9 |
| Color | ← Water-White → | |
| pH | 1.3 | 1.2 |
| Free $ClO_2$, *ppm | 2226 | 1956 |

*Equivalent

It can be seen from the above examples that $ClO_2$ readily interacts with the PVP to give a solution possessing oxidizing properties as evidenced by the KI-sodium thiosulfate test procedure.

EXAMPLE 17

A 10% by weight solution of high molecular weight polyvinylpyrrolidone (K 60) in water was prepared and then saturated again with $ClO_2$ gas from a generator. The solution was allowed to stand for several days at room temperature and then saturated again with $ClO_2$ gas from a generator. The solution was allowed to stand for several more days at room temperature and then saturated again with $ClO_2$. The solution was allowed to sit uncovered for 7 days in a hood and the solution was then assayed. The total $ClO_2$ content was 2044 ppm and the free $ClO_2$ content was 1700 ppm, indicating an equivalent $ClO_2$ content of 344 ppm for the PVP-$ClO_2$ reaction product.

The solution, when analyzed, was a bright chartreuse, indicating that little or no diffusion of $ClO_2$ into the atmosphere had occurred. This behavior is unusual since 10% solutions of the lower molecular weight PVP will rapidly lose $ClO_2$ when uncovered, usually overnight. This data indicates that either the diffusion of $ClO_2$ through the polymer solution was slowed due to high viscosity of the solution or that its vapor pressure was lowered by complexing with the PVP. These observations suggest a method of shipping free $ClO_2$ solutions without the usual attendant loss from water solutions.

EXAMPLE 18

Tests were conducted on the biocidal properties of a solution prepared by reacting $ClO_2$ with a 10% solution of PVP prepared as described in Example 6. The sample assayed at 308 ppm free $ClO_2$ equivalent, and had a pH of 1.9. To 4.5 ml. of this sample (used as is, not diluted) 0.5 ml. of the test organism was added and mixed well. The three test organisms used were Staphylococcus Aureus (ATTC 6538), Psuedomonas Aeruginosa (ATTC 15442), and Samonella Choleraesius (ATTC 10708). The solutions were prepared from slants of the culture to 4 successive propagations in 24 hr broth culture (broth to broth for at least 4 transfers per the AOAC method).

The sample of disinfectant plus organisms was stored at room temperature. At the appropriate time intervals, a loopful of the sample was subcultured into a tube of AOAC broth with Letheen. The subculture tubes were incubated for 48 hours at 35° C. and examined for the presence of growth. The results are recorded in Table VI.

TABLE VI

|  | Minutes | | | | | Hours | | | |
|---|---|---|---|---|---|---|---|---|---|
|  | 1 | 2 | 5 | 10 | 30 | 1 | 2 | 4 | 24 |
| S. Aureus | + | + | + | + | o | o | o | o | o |
| P. Aeruginosa | o | o | o | o | o | o | o | o | o |
| S. Choleraesuis | o | o | o | o | o | o | o | o | o |

+ = growth, o = no growth

The results show that the solution possesses powerful cidal activity, killing *S. Aureus* in greater than 10 but less than 30 minutes and *P. Aeruginosa* and *S. Choleraesuis* in less than 1 minute. For comparison, a solution of Anthium Dioxcide (5% solution of stabilized $ClO_2$) which had been diluted to 1:140 (357 ppm total $ClO_2$) and adjusted to pH 4.0 had the following kill times for analogous organisms; *S. Aureus* (ATTC 6538) - 20 min., *Samonella Choleraesius* (ATCC 7001) 5 min.

In order to demonstrate that the kill of microorganisms was not related only to the pH of the test solution being below 2.0, and that the solution is still a powerful biocide at higher pH levels, another sample of the solution was tested after its pH had been adjusted to 5.98 with NaOH. The results of these tests, which were carried out using the same procedure, are given in Table VII.

TABLE VII

|  | Minutes | | | | | Hours | | | |
|---|---|---|---|---|---|---|---|---|---|
|  | 1 | 2 | 5 | 10 | 30 | 1 | 2 | 4 | 24 |
| S. Aureus | + | + | + | + | + | + | + | o | o |
| P. Aeruginosa | + | + | + | o | o | o | o | o | o |
| S. Choleraesuis | + | + | + | + | o | o | o | o | o |

The data in Table VII show that upon increasing the pH to 5.98, while the cidal activity is diminished slightly, the solution is still a powerful biocide.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. An organically stabilized chlorine dioxide composition which exhibits biocidal activity, said composition being comprised of a $ClO_2$ product which has been prepared by water soluble polymeric N-vinyl pyrrolidone.

2. The composition of claim 1, wherein the $ClO_2$/polymer product is prepared from an aqueous mixture of chlorine dioxide and a polymeric N-vinyl pyrrolidone.

3. The composition of claim 2, wherein the chlorine dioxide is present in the aqueous mixture in excess of the amount capable of reacting or complexing with the polymeric N-vinyl pyrrolidone.

4. The composition of claim 1, wherein the polymeric N-vinyl pyrrolidone has a K value in the range of about 10 to 90.

5. The composition of claim 4, wherein the polymeric N-vinyl pyrrolidone has a K value of about 15 or less.

6. The composition of claim 4, wherein the polymeric N-vinyl pyrrolidone has a K value in the range of about 25 to 50.

7. The composition of claim 4, wherein the polymeric N-vinyl pyrrolidone has a K value in the range of about 75 to 90.

8. A composition, useful as a biocide, which is prepared by the steps of:
   (a) preparing an aqueous solution of a polymeric N-vinyl pyrrolidone,
   (b) saturating the solution with chlorine dioxide,
   (c) allowing the mixture to react to form a $ClO_2$/polymer product wherein the $ClO_2$ is bound to the polymer, removing the excess free chlorine dioxide, and
   (d) adjusting the pH of the resulting solution to a pH of about 4.0 to 6.0.

9. The composition of claim 8, wherein the polymeric N-vinyl pyrrolidone has a therapeutically effective molecular weight.

10. The composition of claim 9, wherein the aqueous solution contains about 10 to 60% by weight of the N-vinyl pyrrolidone having a K value in the range of about 10 to 90.

11. The method of claim 10, wherein the pH of the saturated solution is raised from about 1.5 to 7.

12. The method of claim 11, wherein the pH of the saturated solution is raised to about 5 or 6.

13. The method of claim 11, wherein the pH is raised by the addition of an inorganic base or an organic base.

14. A method for preparing a cidal composition, which comprises the steps of:
   (a) dissolving a polymeric N-vinyl pyrrolidone in water,
   (b) saturating the aqueous solution with chlorine dioxide,
   (c) allowing the two components to interact to thereby form a $ClO_2$/polymer product wherein the $ClO_2$ is bound to the polymer, and optionally adjusting the pH in the range of from 4 to 7.

15. A method for preventing the growth of microorganisms, which comprises treating the microorganisms with a composition comprising the reaction product of chlorine dioxide and water soluble polymeric N-vinyl pyrrolidone.

16. The method of claim 15, wherein the composition is an aqueous solution of polymeric N-vinyl pyrrolidone saturated with chlorine dioxide.

17. The method of claim 16, wherein the solution contains from about 10 to 60% by weight of polymeric N-vinyl pyrrolidone.

18. The method of claim 16, wherein the polymeric N-vinyl pyrrolidone has a K value in the range of about 10 to 90.

19. The method of claim 16, wherein the microorganism is a bacteria, a fungi, a virus, a spore, or mixture thereof.

20. The method of claim 19, wherein the microorganism is a bacteria.

21. The method of claim 20, wherein the bacteria is selected form the group consisting of gram-negative or gram-positive bacteria, or mixture thereof.

* * * * *